United States Patent [19]

Miller et al.

[11] Patent Number: 5,075,550

[45] Date of Patent: Dec. 24, 1991

[54] INFRARED DETECTOR FOR HYDROGEN FLUORIDE GAS

[75] Inventors: David C. Miller, Downers Grove; Arthur R. Brown, Warrenville, both of Ill.

[73] Assignee: Amoco Corporation, Chicago, Ill.

[21] Appl. No.: 552,242

[22] Filed: Jul. 12, 1990

[51] Int. Cl.$^5$ .......................................... G01N 21/35
[52] U.S. Cl. ................................ 250/338.5; 250/339; 250/343
[58] Field of Search .................... 250/338.5, 339, 343

[56] References Cited

U.S. PATENT DOCUMENTS

| | | | |
|---|---|---|---|
| 4,501,968 | 2/1985 | Ebi et al. | 250/343 |
| 4,535,241 | 8/1985 | Eberhardt | 250/339 |
| 4,632,563 | 12/1986 | Lord, III | 250/343 X |
| 4,641,973 | 2/1987 | Nestler et al. | 250/343 X |
| 4,673,812 | 6/1987 | Yoneda | 250/343 X |
| 4,701,395 | 10/1987 | Wronski | 430/58 |

FOREIGN PATENT DOCUMENTS 2304862 10/1976 France .

OTHER PUBLICATIONS

Herget et al., "Infrared Gas Filter Correlation Instrument for In Situ Measurement of Gaseous Pollutant Concentrations", Applied Optics, vol. 15, No. 5, May 1976, pp. 1222-1228.

Primary Examiner—Constantine Hannaher
Assistant Examiner—Edward J. Glick
Attorney, Agent, or Firm—Thomas W. Tolpin; William H. Magidson; Ralph C. Medhurst

[57] ABSTRACT

The infrared dual beam hydrogen fluoride (HF) gas detector comprises a light source for generating a light beam, a reference filter which passes light at a wavelength in the infrared range, such wavelength light being highly not absorbed by HF gas, an HF sensing filter which passes light at a wavelength in the infrared range, such wavelength light being highly absorbed by HF gas, structure for directing the light beam through a space containing vapor under investigation and alternately through each filter, a first sensor for sensing the light transmitted through the reference filter and for generating a first signal, a second sensor for sensing the light transmitted through the HF sensing filter and for generating a second signal, first circuitry for demodulating and amplifying the first signal generated by light transmitted through the reference filter, second circuitry for demodulating and amplifying the second signal generated by light transmitted through the HF sensing filter, and a comparator for comparing the first demodulated and amplified signal with the second demodulated and amplified signal and for generating an output control signal indicative of the amount of HF gas in parts per million - meters in the vapor in the space under investigation.

10 Claims, 4 Drawing Sheets

INFRARED DETECTOR FOR HYDROGEN FLUORIDE GAS

BACKGROUND OF THE INVENTION

1. Field of the Invention

The present invention relates to an infrared detector for hydrogen fluoride gas and more specifically to a dual-beam gas detector which compares light transmissiveness through a gas that may contain hydrogen fluoride gas and in which the transmission of a light beam though a reference filter having a wavelength which is not highly absorbed by hydrogen fluoride gas is compared with the transmission of a light beam through an hydrogen fluoride sensing filter having a wavelength which is highly absorbed by hydrogen fluoride gas.

2. Description of the related art including information disclosed under 37 CFR §§1.97-1.99.

Hydrogen fluoride gas leaks from hydrogen fluoride alkylation units at refineries are of great concern to the petroleum industry. Also, hydrogen fluoride gas at aluminum smelting sites is of concern to the aluminum industry.

This is particularly so because very small amounts of hydrogen fluoride (HF) gas can cause irritation of the nose, eyes and skin, as well as respiratory irritation. Slightly larger amounts, e.g., 50 ppm-m for a period of 30-60 minutes can cause severe irritation of the eyes, burning of the skin, and lung and cardiovascular collapse leading to death.

Accordingly, at sites where HF gas may be present, periodic tests are conducted to determine the presence of HF gas.

One technique for testing the air is to suck air past a sensitized tape and then to test the tape with colorimetry. This technique is very slow.

Another technique is to utilize an electrochemical gas monitoring device such as a gas monitoring instrument of the type sold by International Sensor Technology c,f Irvine, CA which utilizes "self-consuming" electrochemical and catalytic sensors, and includes a heater and a collector embedded in a metal oxide material Such instruments are expensive, have a slow response time and have a drop-off in accuracy and sensitivity at low concentrations of HF gas, e.g., down to 50 ppm-m.

Also, heretofore, Wright & Wright, Inc dual-beam hydrocarbon detectors have been utilized by the petroleum industry for sensing the presence of hydrocarbons for the purpose of stopping product loss and preventing contamination of the adjacent environment. Such detectors are much less expensive than the electrochemical gas monitoring instruments but, heretofore, have not been utilized for detecting HF gas.

Further, it is known from U.S. Pat. No. 4,701,395 to provide an IR-sensitive photoconductive member comprising a charge transport layer, a semi-conductor superlattice of alternating layers of amorphus silicon and amorphus germanium or other alloys, each 5-100 angstroms thick and having at least 10 periods; a first blocking layer adjacent the first layer of the superlattice and a support layer adjacent the first layer on the blocking layer. Such a photoconductive member exhibits high photosensitivity at wavelengths up to 0.9 microns and is used for the infrared detection of oil spills or hydrocarbons.

Additionally, French Patent No. 2 304 862 discloses a torch-burning hydrocarbon system using a selective infrared radiation pyrometer and a thermistor. A range of radiation from the flame in a torch-burning waste gas is selected together with the value of luminance of this radiation The luminance value selected is at a level below that corresponding to the appearance of black smoke.

Radiation is detected continuously and an electrical signal is generated which is a function of the luminance of the radiation. This signal is used for the automatic control of the injection of steam into the burning waste gas for the purpose of reducing the accidental emission of black smoke.

As will be described in greater detail hereinafter, the hydrogen fluoride gas detector of the present invention differs from the previously proposed techniques for sensing HF gas by utilizing a Wright & Wright, Inc. dual-beam detector modified to include selected reference and sensor filters and enhanced calibration circuitry, thereby to provide an inexpensive, fast response, and high sensitivity HF gas detector which can provide an alarm signal for concentrations of HF gas from 30-50 parts per million meters.

SUMMARY OF THE INVENTION

According to the present invention there is provided an infrared dual beam hydrogen fluoride (HF) gas detector comprises a light source for generating a light beam, a reference filter which passes light at a wavelength in the infrared range, such wavelength light being highly not absorbed by HF gas, an HF sensing filter which passes light at a wavelength in the infrared range, such wavelength light being highly absorbed by HF gas, structure for directing the light beam through a space containing vapor under investigation and alternately through each filter, a first sensor for sensing the light transmitted through the reference filter and for generating a first signal, a second sensor for sensing the light transmitted through the HF sensing filter and for generating a second signal, first circuitry for demodulating and amplifying the first signal generated by light transmitted through the reference filter, second circuitry for demodulating and amplifying the second signal generated by light transmitted through the HF sensing filter, and a comparator for comparing the first demodulated and amplified signal with the second demodulated and amplified signal and for generating an output control signal indicative of the amount of HF gas in parts per million meters in the vapor in the space under investigation.

DESCRIPTION OF THE PREFERRED EMBODIMENT(S)

Figure 1:
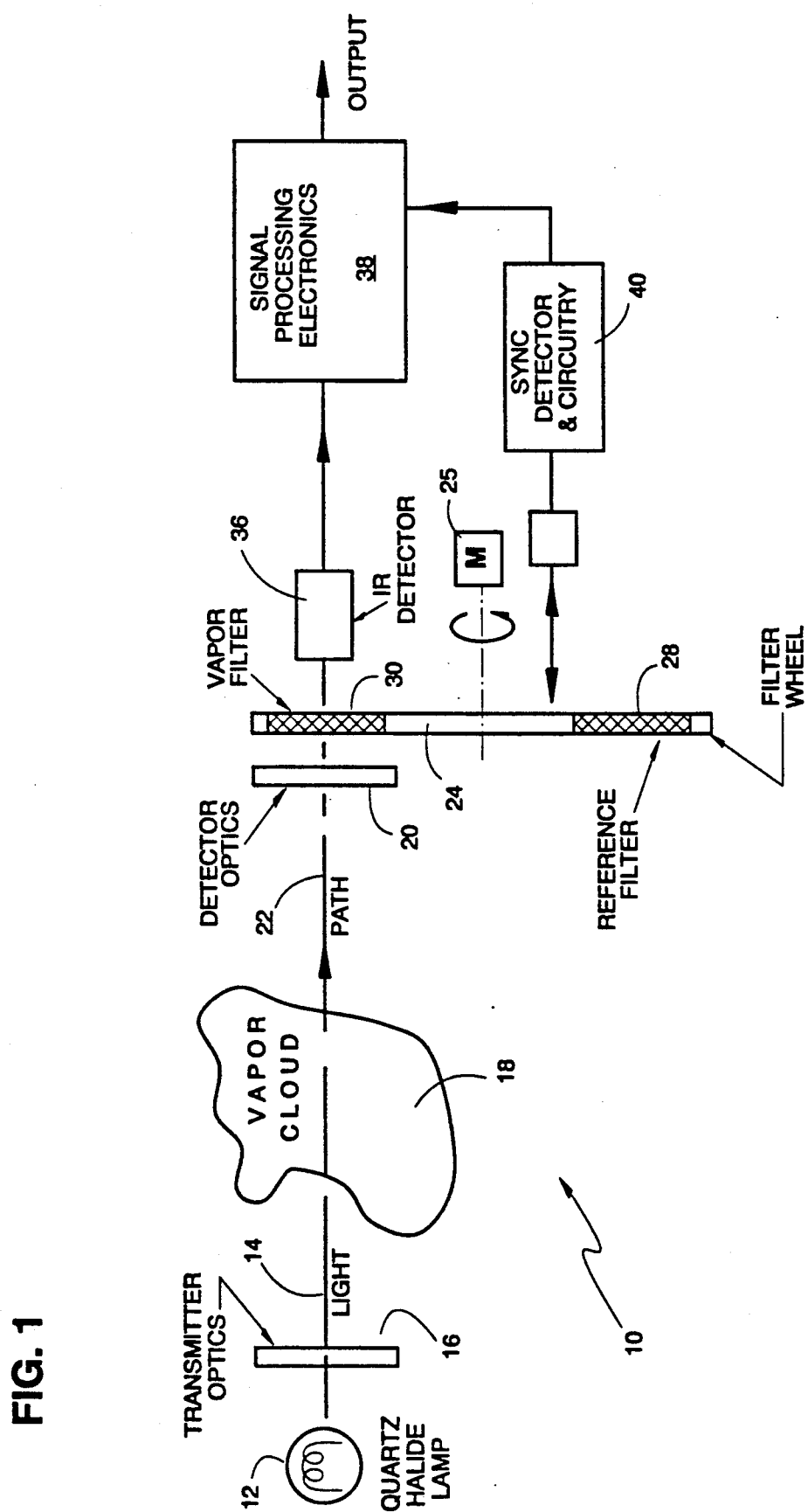
FIG. 1 is a block schematic view of the HF gas detector of the present invention employing a filter wheel

In FIG. 1 there is illustrated a block schematic diagram of a Wright & Wright, Inc. dual-beam gas detector 10 having modified filters and enhanced signal processing electronics according to the teachings of the present invention for enabling such device to be utilized in detecting HF gas The detector 10 includes a quartz halide lamp 12 which emits a light beam 14 that is directed toward and through transmitter optics 16 and then through a vapor cloud 18 under investigation to detector optics 20. A transmitted beam 22 that passes through the detector optics 20, passes through a filter wheel 24 driven by a motor 25, and as the filter wheel 24 rotates, such transmitted beam 22 will pass through two filters. One of the filters 28 is a reference filter 28 and the other filter 30 is an hydrogen fluoride sensing filter 30.

The light beam 32 transmitted through each filter 28 or 30 is supplied to an infrared light detector 36 which then generates a signal that is processed by signal processing electronics 38. If desired, four filters, two filters 28 and two filters 30 can be used.

At the same time, a wheel sensing circuit 40 senses an electric signal from a photodetector 41 which receives (or does not receive) light signals indicative of the instantaneous position of the filter wheel filter 24. In this way, information regarding which filter is in the path of the light beam 22 from the detector optics 20 is determined and passed on to a synchronization detector circuit 42 which is coupled to, and indicates to, the signal processing electronics 38 whether a signal sensed by the signal processing electronics 38 was generated by light passing through the reference filter 28 or the HF sensing filter 30.

Figure 2:
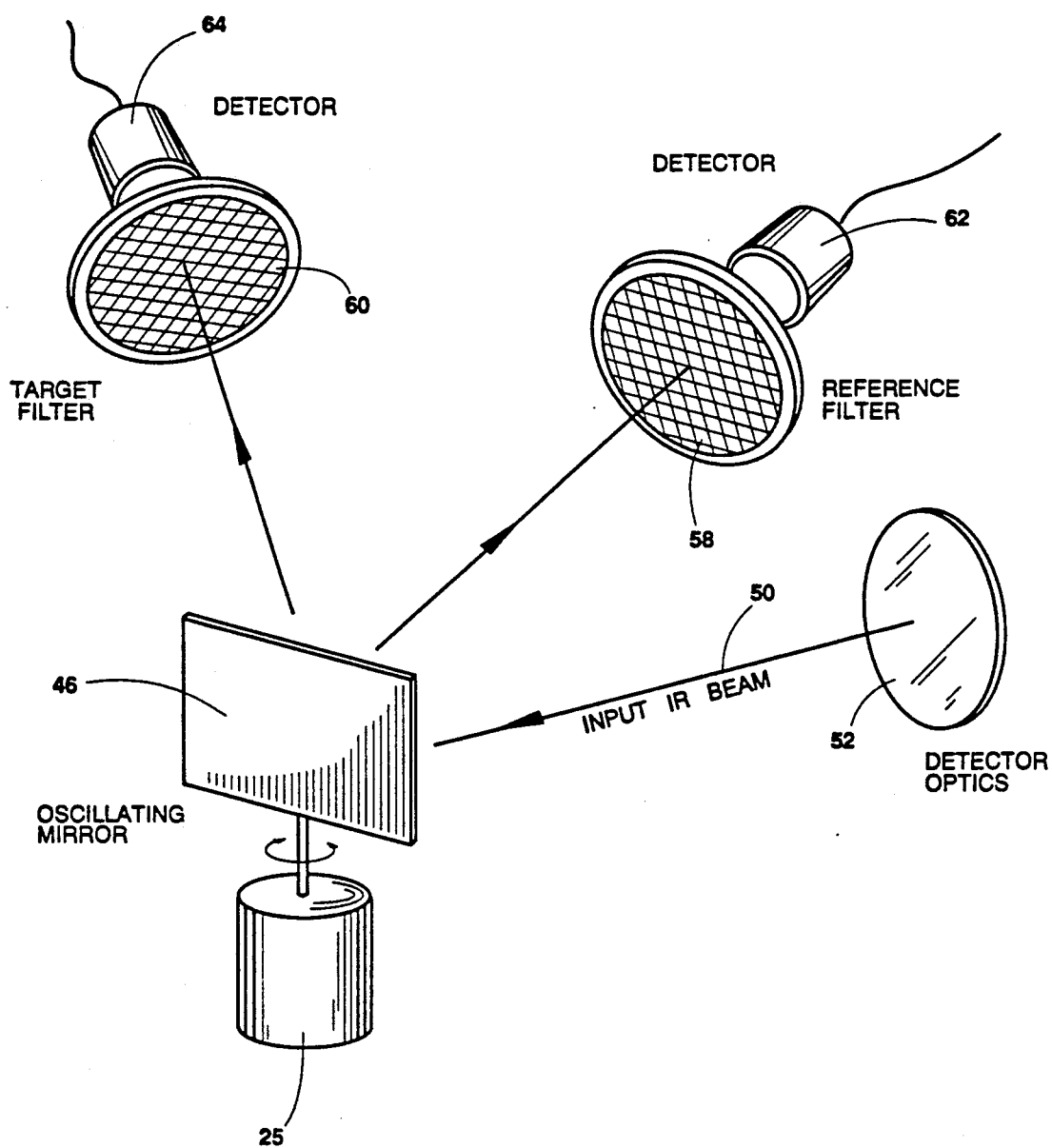
FIG. 2 is a perspective view of a portion of a modified HF gas detector which utilizes two light detectors and a rotating mirror.

As shown in FIG. 2, the motor 25 for rotating the filter wheel 24 can instead oscillate a mirror 46 which receives an input infrared light beam 50 from detector optics 52 and reflects that light beam 50 either to a reference filter 58 or an HF sensing filter 60 each positioned in front of a light detector 62 or 64.

Figure 3:
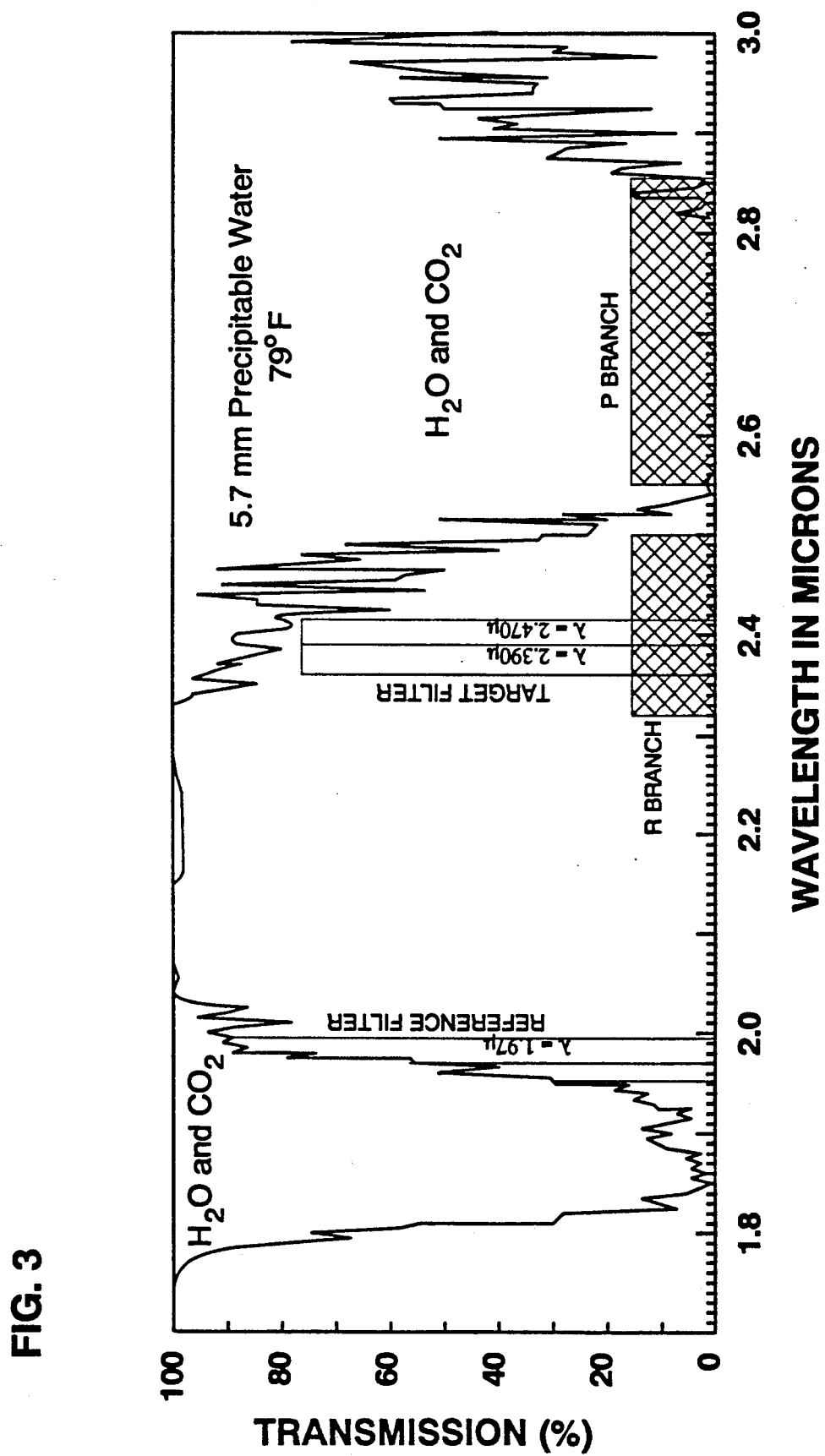
FIG. 3 is a portion of a graph of transmission versus wavelength for light at different wavelengths through a gas comprising water vapor and carbon dioxide and shows selected filter ranges.

According to the teachings of the present invention, and with reference to FIG. 3, a reference filter 28, 58 is chosen having a light transmissiveness at a wavelength which is highly non absorbing of hydrogen fluoride gas, e.g., a wavelength of 1.970 microns. The reference filter 28, 58 is selected to match, with no HF present, the transmission characteristics of the HF sensing filter 30, 60.

Then the HF sensing filter 30, 60 can have a center wavelength at approximately 2.390 microns. Such a filter 30, 60 passes light in the range of 2.39 micron wavelength and blocks other light. The HF sensing filter can also have a center wavelength at 2.47 microns.

As shown in the graph of FIG. 3, this is an area where there is 80-85 percent transmissiveness of light through water vapor and carbon dioxide but is a wavelength at which there is high absorption of light by hydrogen fluoride gas. See the article entitled, "Infrared Spectrum of Hydrogen Fluoride Line Position and Line Shapes, Part II Treatment of Data Results" by Herget, Deeds, Gailar, Lovell and Nielsen which appeared in the October 1962, Vol. 52, No. 10 issue of *JOURNAL OF THE OPTICAL SOCIETY OF AMERICA*, pages 1113-1119.

Suitable filters could include filters at the second harmonic such as an HF sensing filter having a center wavelength of approximately 1.27 microns for sensing infrared light transmissiveness through a gas vapor that may contain hydrogen fluoride gas and a reference filter having a center wavelength of approximately 1.057 microns.

Good results in sensing low concentrations of HF gas in a vapor were obtained utilizing a hydrogen fluoride sensing filter 30, 60 having a center wavelength of 2.390 microns, a band width of 53 nanometers and a reference filter 28, 58 having a center wavelength of 1.970 microns, a band width of 43 nanometers.

Also good results were obtained with an HF sensing filter 30, 60 having a center wavelength of 2.47 microns a band width of 70 nanometers and a reference filter 28, 58 having a center wavelength of 2.950 microns, a band width of 55 nanometers.

Several usable filters are listed below:

| CENTER WAVELENGTH | FILTER WIDTH AT HALF MAXIMUM | BAND |
|---|---|---|
| I. HF SENSING FILTERS | | |
| 2470 nm ± 20 nm | 70 nm ± 10 nm | FUNDAMENTAL |
| 2390 nm ± 20 nm | 60 nm ± 10 nm | |
| 1270 nm ± 10 nm | 80 nm ± 10 nm | (2nd harmonic) |
| II. HF REFERENCE FILTER | | |
| 1970 nm ± 20 nm | 50 nm ± 10 nm | FUNDAMENTAL |
| 1057 nm ± 10 nm | 16 nm ± 4 nm | 2nd harmonic | nm = nanometers

Figure 4:
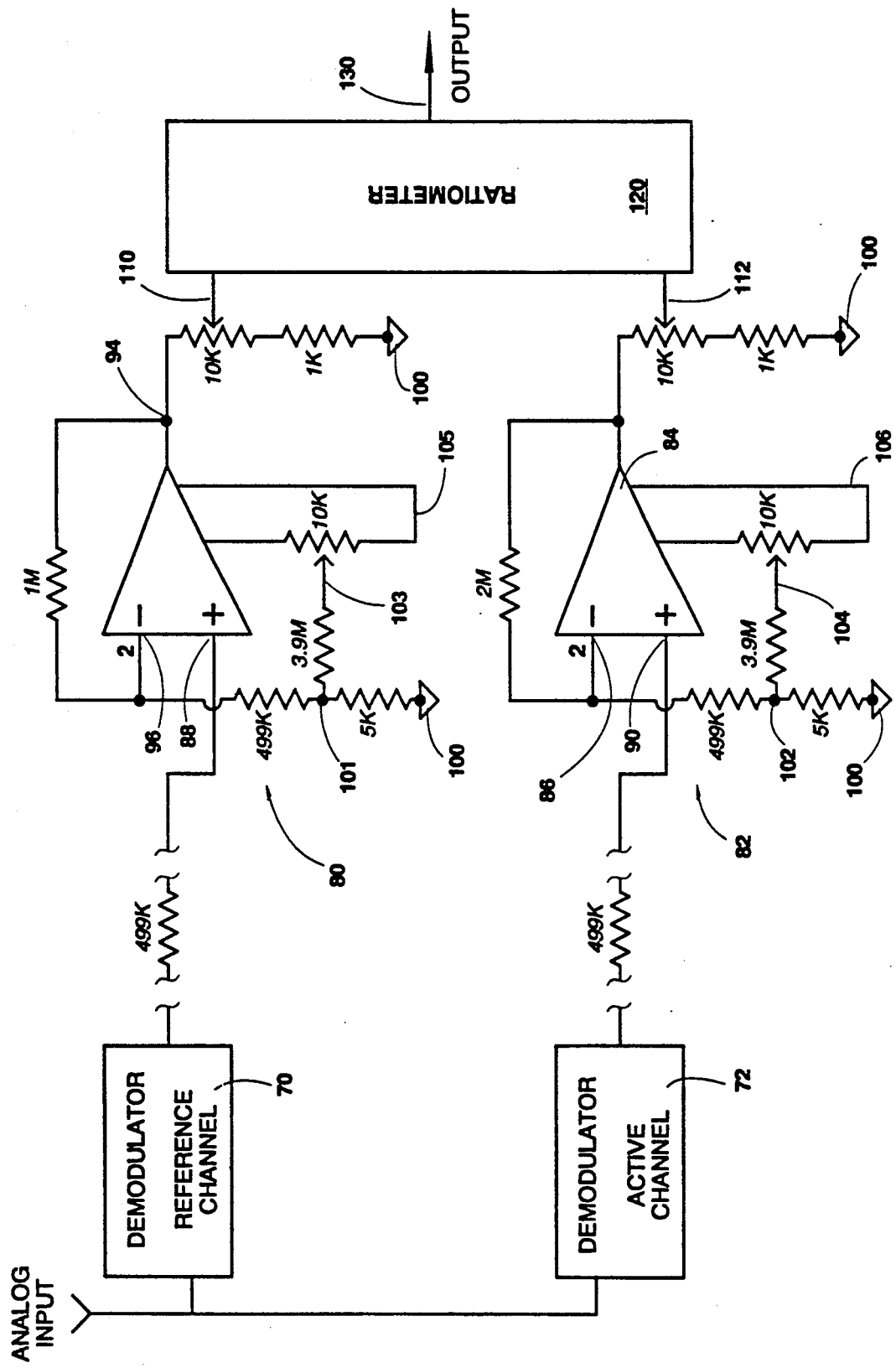
FIG. 4 is a block electrical schematic diagram of the signal processing electronics including demodulator channels, operational amplifiers constructed according to the teachings of the present invention, and a ratiometer which are utilized to provide a meaningful output signal.

Turning now to FIG. 4, the signal processing electronics 38 includes a reference channel demodulator 70, and an active channel demodulator 72, both of which receive analog input signals from the light detector 36 or 62, 64.

According to the teachings of the present invention, the output signal from each demodulator 70, 72 is passed through a 499K ohm resister and then to an operational amplifier 80 or 82. These operational amplifiers 80, 82 are modified from the operational amplifiers provided in a Wright & Wright, Inc. hydrocarbon detector and are very similar except that the operational amplifier 82 connected to the output of the active channel demodulator 72 has a 2M ohm feedback resistor between an output 84 and a minus input 86 of the amplifier 82.

The other operational amplifier 80 has a 1-M ohm resistor connected between an output 94 and a minus input 96 of the amplifier 80.

Also as shown, both operational amplifiers 80, 82 have the output of the demodulator 70, 72 connected to a plus input 88 or 90 of the amplifier 80 or 82. The input to the negative input 86 or 96 of the amplifier 80 or 82 is connected through a 499K ohm and 5K ohm series connected resistors to system common 100 and a junction 101 or 102 between those resistors is connected by a 3.9M ohm resistor to an adjustable contact 103 or 104 of a 10K ohm variable resistor connected to a gain control circuit 105 or 106 for the amplifier 82 or 80.

The output 84 or 94 from each operational amplifier 82 or 80 is connected to two series connected resistors, one being a 10K ohm variable resistor and the other being a fixed 1K ohm resistor. An adjustable potential contact 110 or 112 of each 10K resistor is connected to an input of a ratiometer 120 which compares the relative potentials or voltages from each amplifier 82, 80 and then produces an output signal at an output 130 which can be used to trigger an alarm or annunciator.

Tests with a 2.39 micron wavelength HF sensing filter 30 or 60 and a 1.97 micron reference filter 28 or 58 have shown that a hydrogen fluoride gas detector 10 constructed according to the teachings of the present invention, in the manner described above, can yield sensitivity in parts per million meters of 44 ppm-m. Such a concentration of HF gas causes the detector 10 to output a 100 millivolt output signal and with an anticipated noise signal of ±25 millivolts, results in a good sensing threshold signal.

By selecting and providing in a Wright & Wright, Inc. gas detector, sensing and reference filters in the infrared range, with the sensing filter having a wavelength at which light passing through HF gas is highly absorbed, and the reference filter having a wavelength where HF gas is not highly absorbed and enhanced gain and amplification controlling resistors associated with operational amplifiers in signal processing electronics, a relatively inexpensive, long path, fast response and high HF gas sensitivity, HF gas detector is provided.

From the foregoing description, it will be apparent that the HF gas detector 10 of the present invention provides a number of advantages, some of which have been described above, and others of which are inherent in the invention. Primarily, the HF gas detector 10 provides a relatively inexpensive, high sensitivity and fast response HF gas detector.

Also, it will be apparent &hat modifications can be made to the HF gas detector 10 without departing from the teachings of the present invention. Accordingly, the scope of the present invention is only to be limited as necessitated by the accompanying claims.

We claim:

1. An infrared dual beam hydrogen fluoride (HF) gas detector comprising a light source for generating a light beam, a reference filter which passes light at a wavelength in the infrared range, such wavelength light having a center wavelength of 1970 nanometers ±20 nanometers which is highly not absorbed by HF gas, an HF sensing filter which passes light at a wavelength in the infrared range, such wavelength light being highly absorbed by HF gas and having a center wavelength of 2390 nanometers ±20 nanometers, means for directing the light beam through a space containing vapor under investigation and alternately through each filter, first means for sensing the light transmitted through said reference filter and for generating a first signal, second means for sensing the light transmitted through said HF sensing filter and for generating a second signal, first means for demodulating and amplifying the first signal generated by light transmitted through the reference filter, second means for demodulating and amplifying the second signal generated by light transmitted through the HF sensing filter, and means for comparing the first demodulated and amplified signal with the second demodulated and amplified signal and for generating an output control signal indicative of the amount of HF gas in parts per million - meters in the vapor in the space under investigation.

2. The HF gas detector of claim 1 wherein said means for alternately passing the light beam through the reference filter and the HF sensing filter includes a motor driven filter wheel having an annular portion thereof containing the filters positioned to rotate through the path of the light beam and said first and second sensing means are defined by a single infrared light detector positioned in the path of the transmitted light beam.

3. The HF gas detector of claim 1 wherein said means for alternately passing the light beam through the reference filter and the HF sensing filter includes a motor driven mirror which is oscillated between first and second positions and which is disposed in the path of the transmitted light beam such that in the first position said mirror reflects light to said reference filter and in said second position reflects light to said HF sensing filter, and said first and second sensing means are defined by first and second infrared light detectors each positioned behind one of said filters.

4. An infrared dual beam hydrogen fluoride (HF) gas detector comprising a light source for generating a light beam, a reference filter which passes light at a wavelength in the infrared range, such wavelength light having a center wavelength of 1057 nanometers ±10 nanometers which is highly not absorbed by HF gas, an HF sensing filter which passes light at a wavelength in the infrared range, such wavelength light being highly absorbed by HF gas and having a center wavelength of 1270 nanometers ±10 nanometers, means for directing the light beam through a space containing vapor under investigation and alternately through each filter, first means for sensing the light transmitted through said reference filter and for generating a first signal, second means for sensing the light transmitted through said HF sensing filter and for generating a second signal, first means for demodulating and amplifying the first signal generated by light transmitted through the reference filter, second means for demodulating and amplifying the second signal generated by light transmitted through the HF sensing filter, and means for comparing the first demodulated and amplified signal with the second demodulated and amplified signal and for generating an output control signal indicative of the amount of HF gas in parts per million - meters in the vapor in the space under investigation.

5. The HF gas detector of claim 4 wherein said means for alternately passing the light beam through the reference filter and the HF sensing filter includes a motor driven filter wheel having an annular portion thereof containing the filters positioned to rotate through the path of the light beam and said first and second sensing means are defined by a single infrared light detector positioned in the path of the transmitted light beam.

6. The HF gas detector of claim 4 wherein said means for alternately passing the light beam through the reference filter and the HF sensing filter includes a motor driven mirror which is oscillated between first and second positions and which is disposed in the path of the transmitted light beam such that in the first position said mirror reflects light to said reference filter and in said second position reflects light to said HF sensing filter, and said first and second sensing means are defined by first and second infrared light detectors each positioned behind one of said filters.

7. An infrared dual beam hydrogen fluoride (HF) gas detector comprising a light source for generating a light beam, a reference filter which passes light at a wavelength in the infrared range, such wavelength light having a center wavelength of 1970 nanometers ±20 nanometers which is highly not absorbed by HF gas, an HF sensing filter which passes light at a wavelength in the infrared range, such wavelength light being highly absorbed by HF gas and having a center wavelength of 2470 nanometers ±20 nanometers, means for directing the light beam through a space containing vapor under investigation and alternately through each filter, first means for sensing the light transmitted through said reference filter and for generating a first signal, second means for sensing the light transmitted through said HF sensing filter and for generating a second signal, first means for demodulating and amplifying the first signal generated by light transmitted through the reference filter, second means for demodulating and amplifying the second signal generated by light transmitted through the HF sensing filter, and means for comparing the first demodulated and amplified signal with the second demodulated and amplified signal and for generating an output control signal indicative of the amount of HF gas in parts per million - meters in the vapor in the space under investigation.

8. The HF gas detector of claim 7 wherein said means for alternately passing the light beam through the reference filter and the HF sensing filter includes a motor driven filter wheel having an annular portion thereof containing the filters positioned to rotate through the path of the light beam and said first and second sensing means are defined by a single infrared light detector positioned in the path of the transmitted light beam.

9. The HF gas detector of claim 7 wherein said means for alternately passing the light beam through the reference filter and the HF sensing filter includes a motor driven mirror which is oscillated between first and second positions and which is disposed in the path of the transmitted light beam such that in the first position said mirror reflects light to said reference filter and in said second position reflects light to said HF sensing filter, and said first and second sensing means are defined by first and second infrared light detectors each positioned behind one of said filters.

10. An infrared dual beam hydrogen fluoride (HF) gas detector comprising a light source for generating a light beam, a reference filter which passes light at a wavelength in the infrared range, such wavelength light being highly not absorbed by HF gas, an HF sensing filter which passes light at a wavelength in the infrared range, such wavelength light being highly absorbed by HF gas, means for directing the light beam through a space containing vapor under investigation and alternately through each filter, first means for sensing the light transmitted through said reference filter and for generating a first signal, second means for sensing the light transmitted through said HF sensing filter and for generating a second signal, first means for demodulating and amplifying the first signal generated by light transmitted through the reference filter, second means for demodulating and amplifying the second signal generated by light transmitted through the HF sensing filter, and means for comparing the first demodulated and amplified signal with the second demodulated and amplified signal and for generating an output control signal indicative of the amount of HF gas in parts per million - meters in the vapor in the space under investigation, said first means for demodulating and amplifying said first signal comprising a first demodulator coupled to the output of said first sensing means and a first operational amplifier coupled between said first demodulator and said comparing means and including a 499K ohm resistor coupled between said first demodulator and a plus input of said amplifier, a gain control circuit coupled to said amplifier and including a 10K ohnm variable resistor, a 1M ohm feedback resistor connected between an output of said amplifier and a minus input of said amplifier, a 499K ohm resistor and a 5K ohm resistor being series connected between said minus input and a system common, the junction between said resistors being connected through a 3.9M ohm resistor to an adjustable contact of said 10K ohm variable resistor in said gain control circuit, and a 10K ohm variable resistor and a 1K ohm resistor being series connected between said output of said amplifier and system common, and an adjustable contact of said 10K ohm resistor being connected to an input of said comparing means, said second demodulating and amplifying means comprising a second demodulator coupled to the output of said second sensing means and a second operational amplifier coupled between said second demodulator and said comparing means and including a 499K ohm resistor coupled between said second demodulator and a plus input of said amplifier, a gain control circuit coupled to said amplifier and including a 10K ohm variable resistor, a 2M ohm feedback resistor connected between an output of said amplifier an a minus input of said amplifier, a 499K ohm resistor and a 5K ohm resistor being series connected between said minus input and a system common, the junction between said resistors being connected through a 3.9M ohm resistor to an adjustable contact of said 10K ohm variable resistor in said gain control circuit, and a 10K ohm variable resistor and a 1K ohm resistor being series connected between said output of said amplifier and system common, and an adjustable contact of said 10K ohm resistor being connected to an input of said comparing means, said comparing means being defined by a ratiometer.

* * * * *

UNITED STATES PATENT AND TRADEMARK OFFICE
CERTIFICATE OF CORRECTION

PATENT NO.  : 5,075,550

DATED       : December 24, 1991

INVENTOR(S) : David C. Miller, et al

It is certified that error appears in the above-identified patent and that said Letters Patent is hereby corrected as shown below:

| Col. | Line |  |
|------|------|--|
| 1 | 39 | "c,f" should read --of-- |
| 1 | 42 | "material" should read --material.-- |
| 2 | 2-3 | "radiation" should read --radiation.-- |
| 3 | 9 | "gas" should read --gas.-- |
| 3 | 61 | "Fluoride" should read --Fluoride:-- |
| 8 | 16 | "10K ohnm" should read --10K ohm-- |

Signed and Sealed this

Twenty-second Day of June, 1993

Attest:

MICHAEL K. KIRK

*Attesting Officer*  *Acting Commissioner of Patents and Trademarks*